(12) United States Patent
Hagen et al.

(10) Patent No.: US 11,938,293 B2
(45) Date of Patent: Mar. 26, 2024

(54) SELF-RETAINING ENEMA NOZZLE AND AN ENEMA SYSTEM COMPRISING SAID ENEMA NOZZLE

(71) Applicant: Qufora A/S, Allerød (DK)

(72) Inventors: Thit Rose Hagen, Roskilde (DK); Henrik Bork Bjerregaard, Lynge (DK); Ole Hougaard, Helsingør (DK); Lars Monroy, Bagsværd (DK)

(73) Assignee: Qufora A/S, Allerød (DK)

( * ) Notice: Subject to any disclaimer, the term of this patent is extended or adjusted under 35 U.S.C. 154(b) by 0 days.

(21) Appl. No.: 18/041,964

(22) PCT Filed: Aug. 20, 2021

(86) PCT No.: PCT/EP2021/073147
§ 371 (c)(1),
(2) Date: Feb. 16, 2023

(87) PCT Pub. No.: WO2022/038268
PCT Pub. Date: Feb. 24, 2022

(65) Prior Publication Data
US 2023/0270932 A1 Aug. 31, 2023

(30) Foreign Application Priority Data
Aug. 20, 2020 (DK) .............................. PA202070539

(51) Int. Cl.
*A61M 3/02* (2006.01)
*A61M 25/04* (2006.01)
(52) U.S. Cl.
CPC .......... *A61M 3/0279* (2013.01); *A61M 25/04* (2013.01)
(58) Field of Classification Search
CPC .............. A61M 3/0279; A61M 3/0291; A61M 3/0295; A61M 25/04; A61J 15/0015;
(Continued)

(56) References Cited

U.S. PATENT DOCUMENTS

| 2,483,851 A | * | 10/1949 | Charles | ............... A61M 3/0279 604/215 |
| 2002/0019613 A1 | * | 2/2002 | Alexandersen | ....... A61M 3/022 604/279 |

(Continued)

FOREIGN PATENT DOCUMENTS

| GB | 2565640 | 2/2019 |
| GB | 2565640 B | * 10/2019 .......... A61M 3/0279 |

(Continued)

OTHER PUBLICATIONS

International Search Report and Written Opinion for International PCT Patent Application No. PCT/EP2021/073147, dated Oct. 26, 2021 (10 pages).

*Primary Examiner* — Brandy S Lee
*Assistant Examiner* — Hong-Van N Trinh
(74) *Attorney, Agent, or Firm* — Fox Rothschild LLP

(57) ABSTRACT

The present invention relates to a self-retaining enema nozzle (1,1',1",1''') and an enema system (34) comprising said enema nozzle. The enema nozzle (1,1',1",1''') comprises a catheter (2) provided with a retention member (3) arranged for being placed in a compact form during insertion in a body cavity and for being placed in an expanded form for retaining the enema nozzle in said body cavity, and wherein the enema nozzle (1,1',1",1''') further comprises a restriction unit (4) arranged for placing the retention member (3) in its compact form. Since the restriction unit (4) holds, e.g. keeps, places and/or maintains the retention member (3) in the compact form both before and during insertion, any discomfort and/or harm that may be experienced using the conventional enema nozzles/devices is effectively prevented.

23 Claims, 11 Drawing Sheets

(58) Field of Classification Search
CPC .. A61J 15/0038; A61J 15/0023; A61J 15/003; A61B 17/3423
See application file for complete search history.

(56) References Cited

U.S. PATENT DOCUMENTS

2020/0206411 A1    7/2020  Henry et al.
2021/0386926 A1*  12/2021  Lovmar .............. A61M 3/0279

FOREIGN PATENT DOCUMENTS

WO    2009/015152    1/2009
WO    2010/020985    2/2010

\* cited by examiner

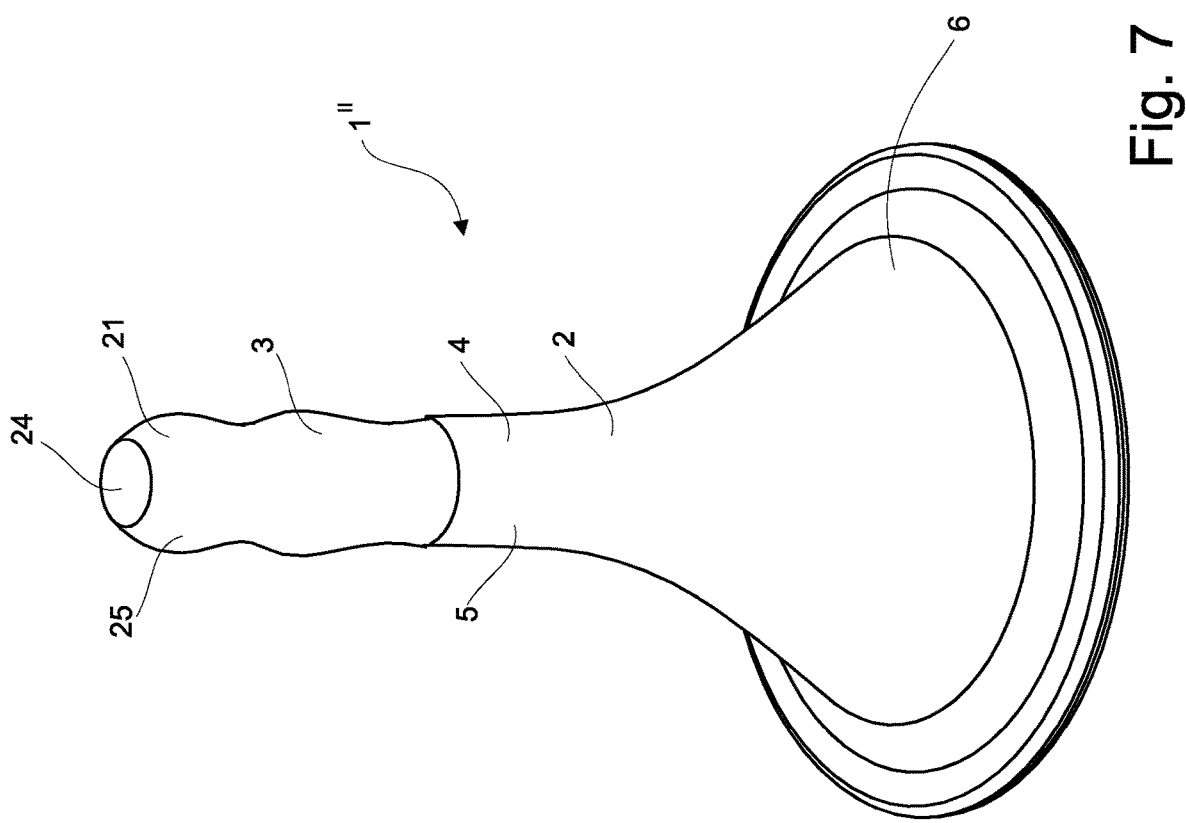

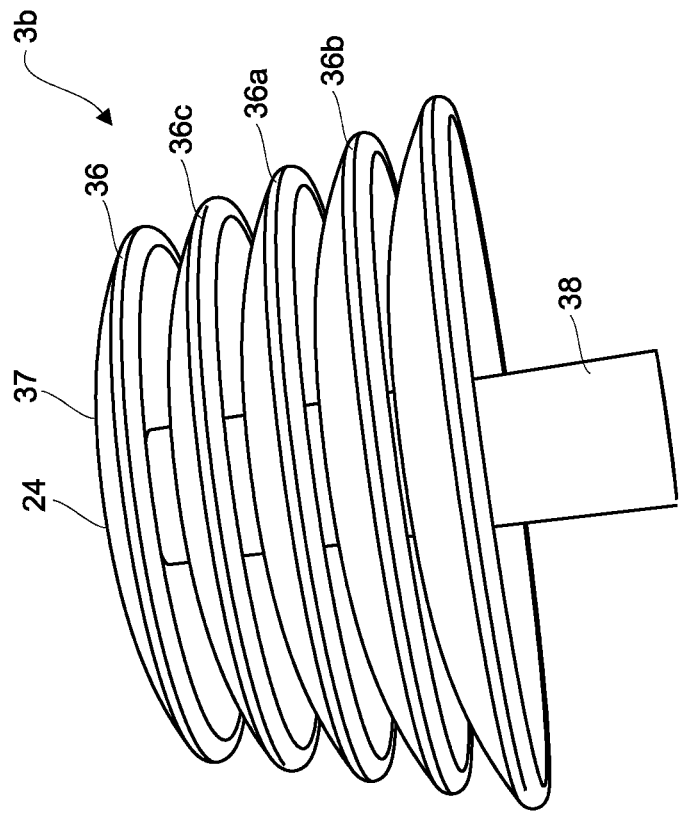
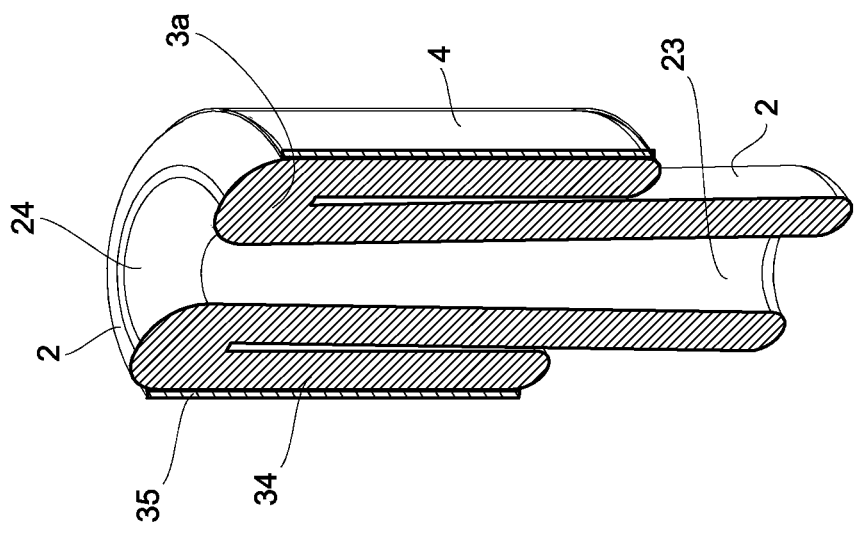
Fig. 16
Fig. 15

SELF-RETAINING ENEMA NOZZLE AND AN ENEMA SYSTEM COMPRISING SAID ENEMA NOZZLE

CROSS-REFERENCES TO RELATED APPLICATIONS

This application is a U.S. National Phase Application of PCT International Application No. PCT/EP2021/073147, filed on Aug. 20, 2021, which is an International Application of and claims the benefit of priority to Danish Patent Application No. PA202070539, filed on Aug. 20, 2020, the entire contents of which are herein incorporated by reference.

The present invention relates to a self-retaining enema nozzle, and an enema system comprising said enema nozzle.

Administrating an enema is a common medical procedure whereby fluid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation.

Enemas are often administered to a patient at home when the need for medical assistance does not necessitate a doctor or another health care assistant. In this respect it is often difficult for the patient to administer the enema liquid to himself or herself since the conventional enema devices often causes discomfort and irritation when being inserted. Moreover, it is difficult for the patient to administer the liquid while steadily holding the enema nozzle in place during the procedure. Often another individual assists the patient but assistance may not always be available, if for instance, the patient lives alone.

In order to overcome these problems a number of enema devices comprise an inflatable balloon for retaining the nozzle in the rectum/colon during administration of the enema has been developed. Such a device is e.g. disclosed in U.S. Pat. No. 5,074,842 which describes an irrigation device having a fixation balloon that is inflated using air, and wherein the air is delivered through a syringe valve communicating with an air passage. A similar system is known from European patent publication no. 1531885, which describes an irrigation device comprising a liquid reservoir and an air-inflated balloon for fixation of a tubular part inserted in the rectum.

Since air is used to inflate the balloon in these known devices, additional elements are needed in the devices in order to ensure that the air can be taken from the surroundings during the inflation procedure, and again vented to the surroundings (instead of into the body cavity) when the irrigation is completed. If the air in the balloon is delivered to the rectum and/or bowel before the nozzle is removed from the rectum, this result in an additional distending or dilation of the colon resulting in pain and discomfort for the patient. Furthermore, use of an air-filled balloon has the problem that the balloon will react to the body movements, e.g. peristaltic reflexes, whereby the nozzle inconveniently may be displaced causing leakage.

In order to overcome these drawbacks some enema devices, see e.g. WO2011023196, uses liquid to inflate the balloon. However, even though the balloon in this system will assist the patient by keeping the enema nozzle inside the rectum during the enema administration procedure, said device has the problem that if the balloon is overfilled the balloon may rupture causing damage to the fragile wall of the rectum and leakage of the liquid filled content of the colon/rectum, and if the balloon is inflated too little it cannot safely keep the enema nozzle in place during use. This is not only unwelcoming for the patient but also very demeaning, as the surroundings inevitability will be contaminated with irrigation liquid and bodily excretions if the enema nozzle unintentionally falls out. As some users of enema devices have no sensory function in the rectum they may not even register if the device falls out.

The self-administration of enema using the conventional enema systems with inflatable balloons with either water or liquid may furthermore be especially difficult for elderly or patients having physical problems, not only due to the complexity of the systems but also since the systems require the use of many different components to work together. The catheter needs to be inserted, the balloon must be inflated, the pump must be activated and the correct dose of liquid must be delivered, and finally the balloon must be deflated before the enema device can be safely removed from the rectum. Thus, not only is the conventional devices difficult to use, e.g. by users with reduced hand function, but the complexity of the systems also make the devices expensive and time-consuming to use.

SUMMARY

It is therefore a first aspect of the present invention to provide an enema nozzle and an enema system that in a fast and efficient manner can be retained in the rectum during an enema administration procedure without the use of an inflatable balloon.

It is a second aspect of the present invention to provide an enema nozzle and an enema system that will speed up the retention procedure and will demand less physical effort when using the enema system.

It is a third aspect of the present invention to provide an enema nozzle and an enema system that safely and effectively can be inserted and removed into a body cavity without causing harm and/or discomfort.

It is a fourth aspect of the present invention to provide an enema nozzle and an enema system that is inexpensive to manufacture and is simple and reliable to use, and therefore can be used for self-administration of an enema e.g. at home.

These and further aspects are achieved according to the present invention by providing an enema nozzle for an enema system, and wherein said enema nozzle comprises a catheter provided with a retention member arranged for being placed in a compact form during insertion in the body cavity and for being placed in an expanded form after insertion for retaining the enema nozzle in the body cavity, and wherein the enema nozzle further comprises a restriction unit arranged for holding/placing the retention member in its compact form during insertion in the body cavity.

The rectum is a very sensitive area of the human body and must therefore be protected form abrasion, perforation, infection as well as excessive pressure. The restriction unit is therefore preferably configured for at least partly surrounding/encompassing the retention member during insertion in the body cavity, i.e. the retention member is preferably placed, at least partly, inside the restriction unit. Since the restriction unit holds, e.g. keeps, places and/or maintains the retention member in the compact form both before and during insertion, any discomfort and/or harm that may be experienced using the conventional enema nozzles/devices is effectively prevented.

After insertion in the body cavity the restriction unit and the retention member is preferably configured for being displaced in relation to each other, and/or the restriction unit is configured for being at least partly removed from the retention member, thereby allowing the retention member to expand for retaining the enema nozzle in the body cavity.

It is in preferred that the restriction unit, when the retention member is in its compact form is arranged for conforming the retention member to the shape and/or dimensions of the catheter and/or prevent the retention member from extending and/or projecting from the annular outer longitudinal side/surface of the catheter. In this way the retention member, and optionally also the restriction unit will have a outer surface corresponding to and/or overlapping with the outer surface of the catheter, i.e. they will be perceived as being a single unit, thereby effectively preventing abrasion and perforation of the rectal wall during insertion of the enema nozzle since any unnecessary discomfort, e.g. by projecting and/or sharp elements effectively is prevented during insertion.

It is further preferred that the dimensions of the outer circumference of the retention member in its compact form is the same, substantially the same or less than the outer circumference of the catheter e.g. taken in a cross-section at the distal end, i.e. tip, of the catheter. This has the advantage that the user cannot perceive or feel the retention member during insertion.

The retention member may in some embodiments be placed on the outer side of the catheter when the retention member is in compact form, however it is then preferred that said retention member is placed parallel with the longitudinal axis of the catheter such that said retention member takes up as little space as possible.

It is preferred that the enema nozzle is configured such that the retention member and the catheter are different elements of the enema nozzle, and/or that the enema nozzle is configured such that the retention member is inserted in the body opening in the compact form, and that said retention member will not expand, until the catheter is inserted, preferably completely, in the body opening. In this way any discomfort for the user during inserting is completely eliminated.

In order to further prevent any irritation and/or damage to the tissue during insertion/use, it is preferred that no sharp edges is present on the parts of the enema nozzle inserted into the body cavity, including any transition area between the retention member, restriction unit and catheter.

Within the context of the present invention term "compact form" means that the retention member, by means of the restriction unit, is placed in a compact, compressed, folded or otherwise suitable form in which the retention member takes up less space compared to when the retention member is placed in its expanded (unfolded) form.

In the expanded form the largest direct distance of the retention member is substantially larger than the largest width (direct distance) of the retention member in its compact form, whereby the retention member effectively fixates the enema nozzle in a body cavity e.g. the rectum. Within the context of the present invention the term "largest direct distance" means the largest possible diameter or largest possible length/distance between two outer points placed the longest possible distance from each other. It is in this respect preferred that the largest direct distance of the retention member in the expanded form is at least three times the size of the largest direct distance of the retention member in the compact form, preferably at least four time the size and even more preferred at least five times the size of the largest direct distance of the retention member in the compact form.

It is preferred that the retention member is not a balloon arranged for being inflated with a fluid (air or liquid), whereby a very simple and inexpensive system having only a very few components is provided. Furthermore, since the retention member does not have to be inflated/deflated the time-consuming and complicated process of inflating and deflating the balloon is eliminated, thereby providing a fast and reliable method of using the enema nozzle according to the invention and ensuring that said nozzle is securely held in place during the entire administration procedure. Furthermore, the user does not have to worry about adjusting the amount of fluid in the balloon in order to provide the required expansion for retaining the nozzle in the rectum, and the enema nozzle will appear small and harmless especially in comparison to the more complicated enema systems having tubes for inflating/deflating a balloon.

The retention member may be provided in a number of ways, and may e.g. be a mechanical structure and/or a resilient compressible body of a foam material, the only requirement being that the size/dimension of the retention member can be restricted by the restriction unit before and during insertion in the body cavity, and that the retention member can expand after insertion.

In a preferred embodiment the retention member in its compact form has a substantially longitudinal structure with a longitudinal axis placed in parallel with the longitudinal axis of the catheter by means of the restriction unit, and wherein said retention member extend outwardly from the longitudinal axis of the catheter in its expanded form thereby serving as an anchor to hold the enema nozzle within the body cavity.

The retention member may in one embodiment comprise one or more expandable structures including, but not limited to posts, wings, fins, pigtail loop(s), struts, plugs, and/or disc(s) which in the compact form can be folded or placed around an outer surface of the catheter by means of the restriction unit. Alternatively the expandable structure may involve an swiveling structure, which is can be opened or closed between the expanded and compact form by rotating a control unit or the like.

In one embodiment the restriction unit is an integral part of the catheter, preferably an internal channel of the catheter, and wherein said internal channel may extend into a distal opening of the catheter. It is furthermore preferred that the retention member is arranged for being displaced or being movably in and/or out of said internal channel such that the retention member projects from and/or withdraws into the distal opening of the catheter.

In order for the user to easily control if the retention member is placed in the compact or expanded form, the enema nozzle and/or enema system according to the invention may comprise a control unit. Said control unit may be arranged such that when the control unit is placed in a first position the retention member is placed in the compact form, and when the control unit is placed in a second position, the retention member is placed in the expanded form. In this way the user can easily activate/adjust the form of the retention member. It is preferred that the control unit comprises a logical indication for changing the form of the retention member. Said control unit may e.g. comprise a stop means such that the retention member only can be placed in its compact form or in its expanded form, but not in an intermediate position between said forms.

In a preferred embodiment the retention member is made of a material capable of conforming to the shape of the colon and provides a tight fit with the colon wall irrespectively of any deformations, e.g. hemorrhoids, fistulas, and/or abscesses in the colon. Furthermore, the tight fit between the retention member and the colon will efficiently provide a seal, and prevent premature and unwanted leakage of fluid and fecal matter from e.g. the anus during an irrigation session.

In a preferred embodiment the retention member is made of an elastic material, preferably having a shape memory, i.e. it will automatically expanded when it is no longer restricted by the restriction unit. This allows the enema nozzle to be securely retained within the body cavity and additionally resists forces applied by bodily fluids, waste and/or excrement that would tend to urge the catheter out of the body opening after it has been inserted.

The retention member may in a preferred embodiment be made of the same material as the catheter, preferably one or more elastomeric polymers, e.g. selected from the group consisting of thermoplastic elastomers (TPE), polyurethane (PU), polyethylene (PE), polyvinyl chloride (PVC), silicone, styrene ethylene butylene styrene (SEBS), thermoplastic polyester elastomer (TPC), thermoplastic styrenic elastomer (TPS), and other similar polymers. The elasticity of the retention member can be altered, e.g. by changing the length of the polymer chains, creating branched chains from linear polymer chains, cross linking the polymer chains and/or adding plasticizers into the polymer.

In one preferred embodiment the retention member comprises an expandable loop preferably made of an elastic material with a shape memory thereby ensuring that a loop shape is obtained. The inventors of the present invention have found that such a loop shape is especially advantageously for retaining an enema nozzle in the rectum/colon.

Before use and during insertion, the loop may be placed inside the internal channel forcing the loop into a folded form, i.e. into a compact form where the longitudinal axis of the loop is parallel with the longitudinal axis of the catheter. The tip of the loop may in one embodiment extend out of the distal opening of the restriction unit thereby providing a flexible insertion tip. In this compact form the catheter with the retention member can easily be inserted into the rectum or other body cavity of the user without risking damage to the rectum and/or colon wall.

When the catheter has been inserted into the body cavity, the loop is forced out of the distal opening, preferably in response to an operation of a control unit, allowing the expandable loop to expand into the desired loop shape by its own inherent elasticity ensuring that the catheter/enema nozzle is retained in the body cavity.

When the desired dosage of enema has been administered, the operator may in one embodiment activate the control unit thereby pulling the loop back into the internal channel, whereby the expandable loop is folded, allowing a simple and easy removal of the enema nozzle according to the invention. In an alternative embodiment the user can simply pull the enema nozzle out, during which the loop will fold in upon itself due to the elastic nature of the loop.

The specific loop shape in its expanded form may be any convenient shape, e.g. a substantially round or oval shape. It is however preferred to provide a loop with square, rhombus or diamond shape, having rounded corners that may function as anchors in the body cavity e.g. rectum/colon.

The end(s) of the loop may in a preferred embodiment pass through the internal channel into the control unit to which the ends of the loop are attached so that the ends of the loop either concurrently or individually can be moved to alter the shape of the loop outside the distal opening. In one embodiment the control unit comprises a cylinder which a user can activate manually, e.g. by axially displacing the cylinder inside the internal channel in the longitudinal direction of the catheter. Such a displacement will cause either expansion or contraction of the loop depending on the displacement direction. When the control unit is advanced axially, i.e. toward the distal end of the catheter, the loop projects from the distal opening and expands in a loop shape by its own elasticity. When the control unit is retracted axially, the loop is pulled into the internal channel and folded. The user can therefore in an easy and fast manner control the form of the expandable loop. In an alternative embodiment the control unit comprises a plunger mechanisms or a control member slidable along a handle, however the principals of advancing or retracting the loop are the same.

The internal channel may in one embodiment be the catheters flow channel, and the distal opening may be the delivery opening. However in a simple and inexpensive embodiment, the enema is delivered via an internal flow channel in the cylinder of the control unit. Said flow channel ends on one or more first delivery openings, which in a position of administering the enema, i.e. when the expandable loop is placed in the extended form are in fluid communication with respective second delivery openings arranged in the catheter for delivering the enema to the rectum/colon.

In an alternative embodiment the enema flow channel is provided within the expandable loop, i.e. said loop is a tube arranged for delivering the enema via one or more delivery openings placed in the side wall of said tube.

In a modified version of the enema nozzle according to the invention comprising an expandable loop, the retention member is not restricted by a retention unit, e.g. an internal channel before and during insertion in the rectum. Instead the expandable loop is held in a folded position by the user, during insertion, whereby the expandable loop automatically will expand after insertion when the user releases said loop.

In an alternative embodiment according to the present invention the expandable loop is substituted with a resilient compressible foam body which can be moved out of the internal channel of the catheter in response to an operation of a control unit, which preferably corresponds to the control unit for the expandable loop embodiment. The foam body may in one embodiment be made of a compressible material which is compressed by the inner walls of the internal channel and which therefore automatically will expand when it is forced out of the internal channel. However, in an alternative embodiment, the foam material will expand when it comes into contact with a liquid, e.g. the body fluids/humidity in the body cavity and/or the enema fluid when the enema is administered.

The internal channel in this embodiment may be the flow channel for the enema, but in a preferred embodiment an internal flow channel is arranged inside the foam body and opens into a delivery opening at the top of said foam body. However, if the foam body is made of a porous material; the enema may also be administered to the rectum/colon via the surface and/or sides of said foam body. Such an embodiment is especially relevant if the body tissue is inflamed or otherwise damaged, as the pressure from enema liquid will be distributed over a larger area, thereby reducing any discomfort that the user might otherwise experience.

In an alternative embodiment the retention unit comprises one or more expandable wing(s)/arm(s) and/or disc(s) that are arranged in parallel with the longitudinal axis of the enema nozzle in the compact form, and that in the expanded form extend radially outwardly e.g. in a bent or arcuate shape.

In a preferred embodiment the retention member in the expanded form has a form corresponding to the tip of a Malecot catheter.

Each of the one or more expandable wings/arms and/or discs comprises a distal end and a proximal end which may adjoin or flush with the outer surface of the catheter.

In the expanded form a number of slots/openings between the expandable wings/arms and/or discs may be provided, and in a preferred embodiment said slots/openings are used as delivery openings for the enema, thereby providing a simple and inexpensive embodiment.

Said one or more expandable wings/arms and/or discs may be moved between the compact and expanded form by means of the control unit. Said control unit may in this embodiment be a simple pulling/pushing mechanism, e.g. comprising one or more wires(s) connected to the distal end of the enema nozzle and/or the expandable wings/arms and/or discs, such that when the user pulls in the wire(s) the expandable wings/arms and/or discs are forced into their radially outwardly expanded form, ensuring that the enema nozzle securely can remain in place during administration of the enema. When the desired dosage of enema has been administered, the user can then push the wire, if desired, whereby the wings/arms and/or discs are substantially straightened and become compact, whereby the enema nozzle easily can be removed from the body cavity.

In a still further embodiment the restriction unit is made of a biodegradable material. Said restriction unit is preferably arranged for restricting the size/dimensions of the retention member before and during insertion, but when the restriction unit comes into contact with the humidity and warmth of the body cavity, the restriction unit is arranged for rapidly dissolving and/or disintegrating.

The biodegradable restriction unit may be a thin cover, a coating, a film, a band, or a hollow cylindrical body having a wall that defines an internal cavity that restricts the size of retention member. Said biodegradable restriction unit may e.g. be perforated and/or comprise a number of openings/slots that ensures that the biodegradable restriction unit may be degraded faster when it comes into contact with moisture in the colon and/or the body heat.

It is preferred that at least the section of the catheter comprising the retention member is contained in said biodegradable restriction unit, however the retention member may also be placed at least partly inside the restriction unit, or only be placed as a band around the compact retention member, the only requirement being that the retention member is placed in the compact form by means of the restriction unit. In this way the restriction unit will either partly or completely surrounds/encompass the retention member such that the retention member remains in the compact form until the nozzle is inserted in the body opening.

The biodegradable material of the restriction unit is preferably selected to rapidly dissolve or disintegrate upon contact with the moisture in the colon and/or the body heat, examples of such materials may be gelatins, a polyvinylalcohol (PVA) film, and/or a starch. It is preferred that the biodegradable restriction unit is dissolved/disintegrated and the retention member is placed in the expanded form in less than two minutes, preferably less than one minute. Even though the period it takes for the biodegradable restriction unit to be dissolved/disintegrated may vary from person to person, it is possible to adjust e.g. the thickness of the biodegradable restriction unit in order to ensure a substantially uniform degradable period. In any case it is preferred that the thickness of the biodegradable restriction unit is below 0.5 mm, preferably below 0.1 mm.

Once the restriction unit is dissolved/disintegrated the retention member may be allowed to expand to the expanded form. As already discussed for the earlier embodiments, the retention member may in this respect be a mechanical structure held in place by the restriction unit, and/or a resilient compressible foam body of material which is self expandable e.g. when coming into contact with body fluids in the body cavity.

In the latter situation, the restriction unit may compress the foam body until it comes into contact with the body fluids in the colon, which first will dissolve/disintegrate the restriction unit; thereafter the fluid in the colon will expand the foam body to a self-retaining state.

The embodiments comprising a foam body represents particularly simple embodiments according to the invention, as the foam body ensures that the enema nozzle according to the invention not only remains in place during the administration procedure, but also that the expandable foam body conforms to the shape of the colon and provides a tight fit irrespectively of any deformations, e.g. hemorrhoids, fistulas, and/or abscesses in the colon. Furthermore, the tight fit between the foam body and the colon will efficiently prevent premature and unwanted leakage of fluid and fecal matter from the anus during an irrigation session.

In some embodiments the enema nozzle may not be arranged for changing the expanded retention member back to the compact form. However, the inherent elasticity and/or flexibility of the retention member ensure that the enema nozzle easily can be removed from the body cavity, e.g. the rectum, simply by pulling in the enema nozzle. The retention member will automatically be compacted, deformed and/or folded by the internal forces of the colon/rectum wall during the removal process.

The simplicity of the enema system according to the invention ensures that any patient or user, e.g. an elderly person without undue efforts can use the enema nozzle for self-administrating irrigation liquid. Since the retention member is placed in a compact form during insertion use of the nozzle according to the invention will significantly reduce the discomfort and inconvenience of the patient associated with the known systems.

The enema nozzle according to the invention may have any desired shape and dimensions. Said catheter has an insertion part that is inserted into the body opening, and a proximal end that extends into a flared funnel-shaped part, preferably via a smooth transition. The flared funnel-shaped part is preferably arranged for providing a sealing effect with the rectum.

The catheter may have any suitable length, depending on the intended delivery site of the enema in the colon, the longer the insertion part the further into the colon the enema may be delivered.

The retention member is preferably placed at or near the distal end of the enema nozzle, preferably at a position such that the retention member in the expanded form will be placed above the dentate line when inserted into the anal cavity, as this will prevent the retention member from irritating the sensitive nerve endings that may be positioned within the anal canal between the opening and the dentate line, also referred to as a pectinate line. In is in this respect preferred that the one or more delivery openings for expelling/delivering the enema is/are placed in or above the retention member, such that the enema is delivered to the colon above the retention member.

Furthermore, at least the part of the catheter intended for being inserted into the body cavity, including any exposed parts of the retention member and restriction unit, may be coated with a hydrophilic coating, for example either as a full coverage coating or an island coating consisting of hydrophilic dots separated by not-coated areas.

When the hydrophilic coating gets wet, e.g. simply when contacted with water, saline or other liquid swelling medium prior to inserting the enema nozzle, the hydrophilic coating gels and/or swells and confers a friction-reducing surface to the exterior face of the coated section or coated part of the nozzle, thereby aiding in enabling a gentle insertion of the nozzle into e.g. the rectum. The swelled hydrophilic coating is resilient and flexible and this characteristic, together with the remaining liquid absorbing properties of the hydrophilic coating, makes the hydrophilic coating also act as an effective seal against leakage along the length of the tubular distal part and out of the rectum or other body cavity.

The enema nozzle may comprise other features, e.g. a number of one-way valves for preventing back flow into the nozzle etc.

The enema nozzle is arranged for being connected to any suitable delivery container, e.g. a delivery container in a large bed-side irrigation system for the use in medical or hospital facilities and/or a small compact delivery container for home-administration of enema. The nozzle may be removable connected to the delivery container by means of conventional coupling unit. Said coupling unit can e.g. comprise a first coupling part attach to the enema nozzle and a second coupling part attached to the delivery container for providing a fluid communication between the two parts. In an especially simple embodiment the first coupling part is the tube for the first flow channel and the second coupling part is a second tube on the delivery container. Said second tube is preferably adapted for providing a liquid tight fit together with the first tube in order to provide the coupling, e.g. by providing that at least one of the first and second tube is made of a flexible material, such that e.g. the one tube can be placed in the other tube.

Even though the enema nozzle and enema system according to the invention is intended for administering an enema to the colon via the rectum, the enema nozzle and device may also be used for irrigation, cleansing and/or infusion into other body cavity, e.g. artificial stomas and fistulas.

The invention will be explained in greater detail below, describing only exemplary embodiments of the enema nozzle with reference to the drawing, in which

BRIEF DESCRIPTION OF DRAWINGS

The invention will be explained in greater detail below, describing only exemplary embodiments of the enema nozzle with reference to the drawing, in which FIGS. 6-9 shows a third embodiment of an enema nozzle according to the present invention, FIG. 15 shows the retention member of FIG. 13 placed in a second restriction unit, FIG. 16 shows a second alternative embodiment of a retention member.

DETAILED DESCRIPTION

Figure 2:
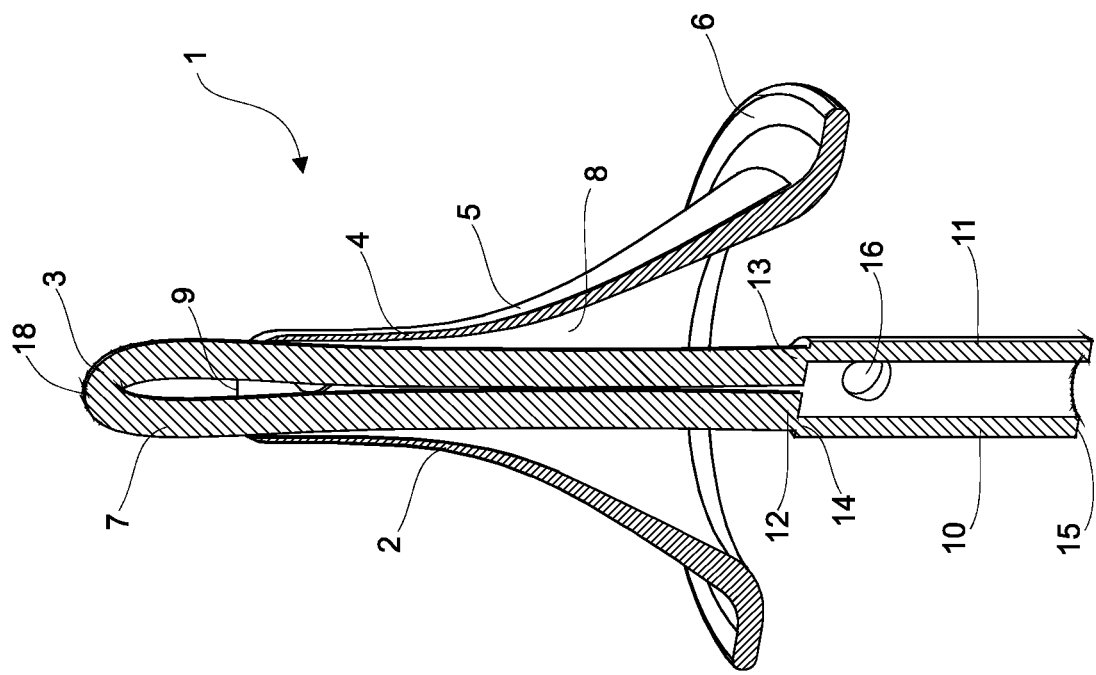
FIGS. 1-4 shows a first embodiment of an enema nozzle according to the present invention.

FIGS. 1-4 show a first embodiment of an enema nozzle 1 according to the invention. Said nozzle consists basically of a catheter 2, a retention member 3 in the form of an expandable loop 7, and a restriction unit 4. The catheter 2 comprises a substantially elongate tubular part 5 defining an insertion body, and a proximal end that extends into a flared funnel-shaped part 6 via a smooth transition.

Figure 1:
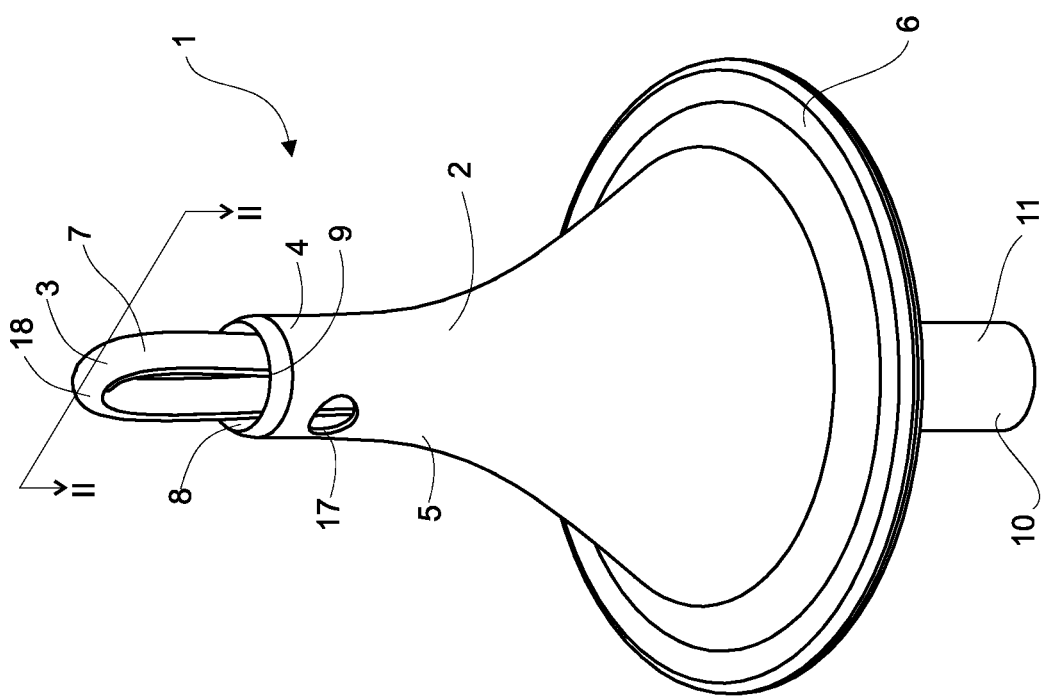

As best shown in FIG. 2, which is a cross-sectional view of FIG. 1 taken along the lines II-II, the restriction unit 4 is defined by an internal channel 8 of the catheter 2 which extends into a distal opening 9, and wherein the retention member 3 is arranged for being movably in and/or out of said internal channel 8 such that the retention member 3 projects from and/or withdraws into the distal opening 9 of the catheter 2 by means of a control unit 10, which in the embodiment shown comprises a cylinder 11.

Figure 3:
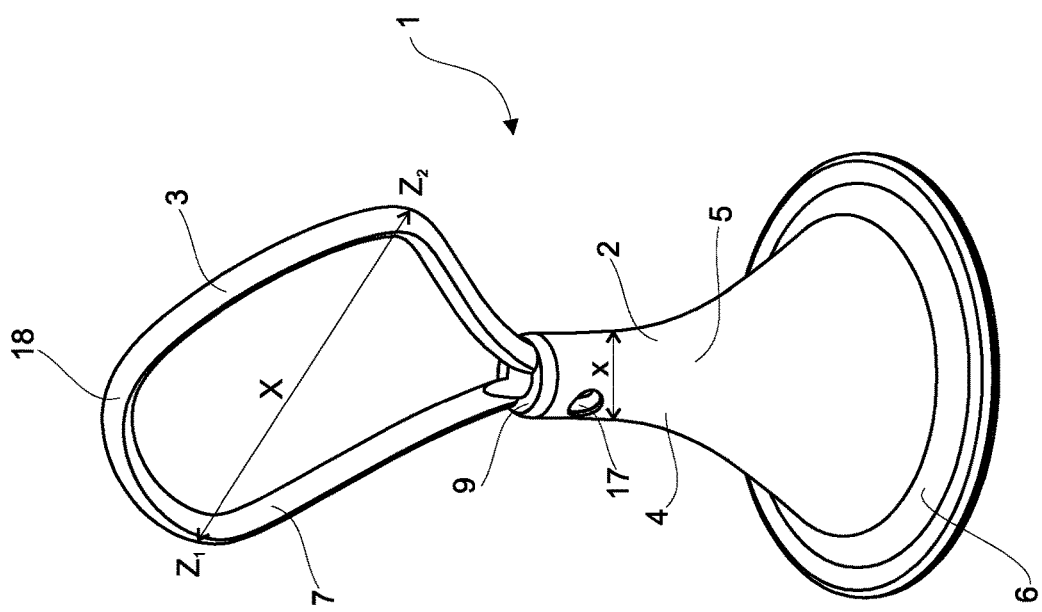

The two ends 12,13 of the expandable loop 8 is attached to the cylinder 11's distal end 14, and the proximal end 15 of the cylinder is arranged for being connected to an enema reservoir and/or enema pump via conventional coupling means, e.g. a snap fitting. Said cylinder 11 comprises two first delivery openings 16, which in a position of administering the enema, i.e. when the expandable loop 7 is placed in the extended form as shown in FIG. 3, will be in fluid communication with two corresponding second delivery openings 17 for delivering the enema to the rectum/colon.

The an expandable loop 7 is in its compact form, as shown in FIGS. 1 and 2, placed inside the internal channel 8 forcing the loop 7 into a folded form, i.e. into a compact form where the longitudinal axis of the loop is parallel with the longitudinal axis of the catheter. The tip 18 of the loop 7 extends out of the distal opening 9 of the internal channel 8 thereby providing a flexible insertion tip i.e. a tip which is softer, more elastic, and more flexible, than the catheter 2, whereby said flexible tip 18 may deform and/or flex in response to deformations and obstacles, during insertion into the rectum and colon. However a person skilled in the art will understand that said loop 7 also could be placed entirely inside the internal channel 8. In any case, in the compact form of the loop 7, the catheter 2 can easily be inserted into the rectum or other body cavity without risking damage to the rectum and/or colon wall.

After the catheter 2 has been inserted into the body cavity, the user can advances the cylinder 11 towards the distal opening 9, e.g. by manually displacing the cylinder 11 (or a tubing connected to said cylinder), thereby axially displacing the cylinder 11 inside the internal channel 9 in the longitudinal direction of the catheter 2, where after the loop 7 projects from the distal opening 9. Since the expandable loop 7 is made of an elastic material with a shape memory the expandable loop 7 will automatically expand into a loop shape, as shown in FIG. 3, by its own elasticity ensuring that the enema nozzle 1 is retained in the body cavity. As is evident from FIG. 3 the largest dimension of retention member, i.e. the largest direct distance X between the two points $Z_1$, $Z_2$ longest from each other, is more than five times the largest diameter (direct distance) x of the tip of catheter 2.

Figure 4:
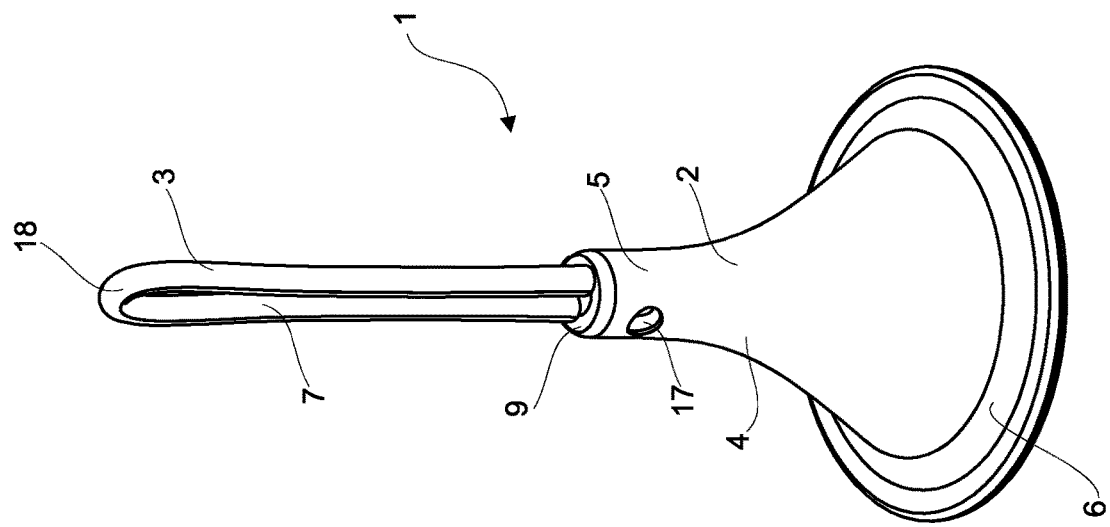

When the desired enema dosage has been delivered to the colon, the loop 7 can either be pulled back into the internal channel 8 returning to the position shown in FIG. 1, by retracting the cylinder 11, or the user can by means of the inherent elasticity of the loop 7 simply pull the enema nozzle 1 out of the rectum, during which the loop 7 will fold in upon itself, as shown in FIG. 4, due to the elastic nature of the loop.

Figure 5:
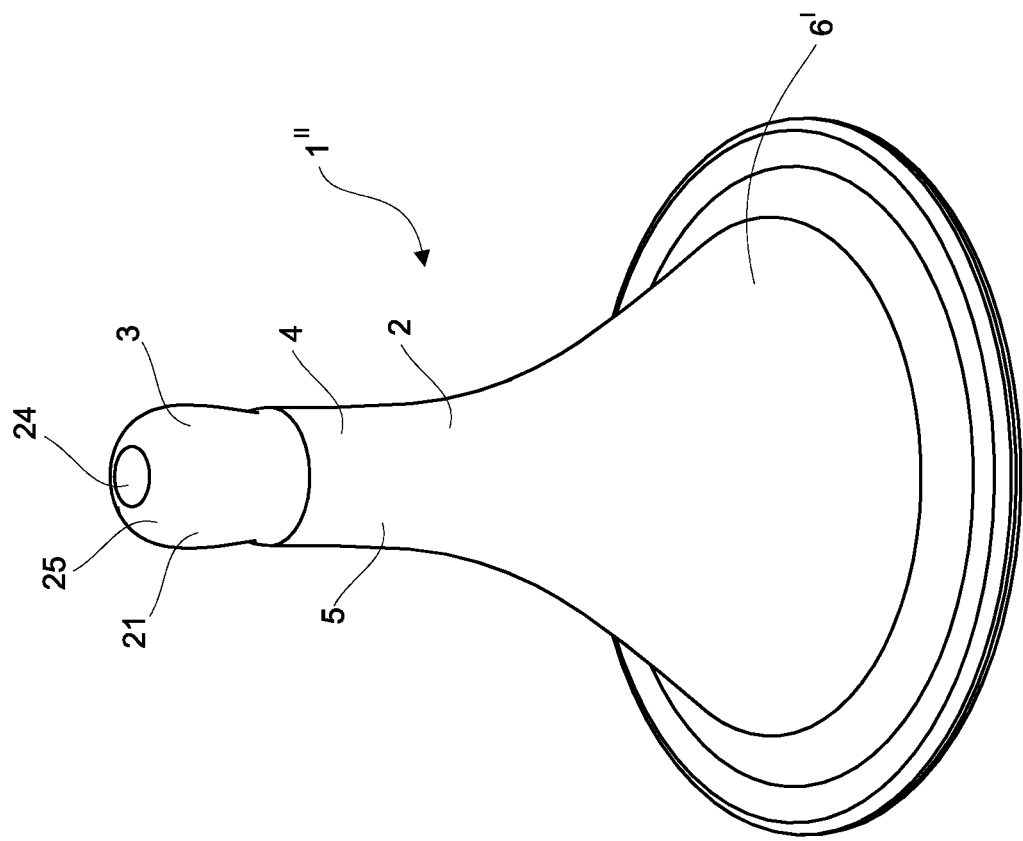
FIG. 5 shows a second embodiment of an enema nozzle according to the present invention.
Figure 6:
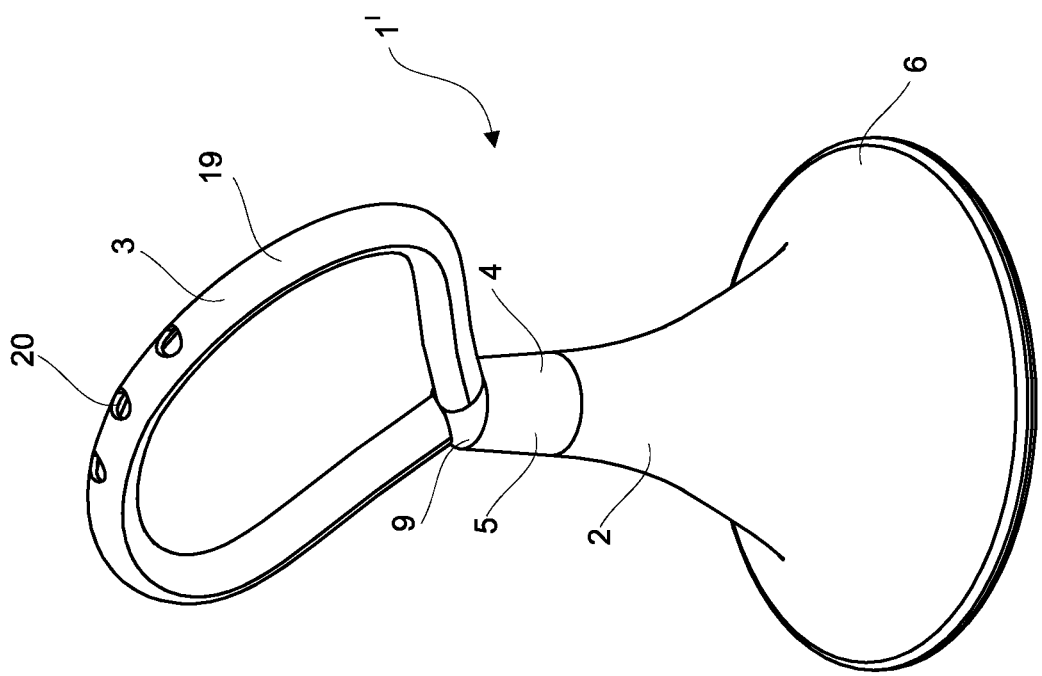

FIG. 5 shows a second embodiment of the enema nozzle 1' according to the present invention. Said embodiment corresponds to the embodiment shown in FIGS. 1-4, and for like parts the same reference numbers are used. The main difference between the first and second embodiment is that instead of delivering the enema via first and second delivery openings 16,17 in the cylinder 11 and catheter respectively, the expandable loop 7 of the second embodiment is a hollow tube 19 arranged for delivering the enema via one or more third delivery openings 20 placed in the side wall of said tube. In the embodiment shown in FIG. 5 the tube comprise three third delivery openings 13.

FIGS. 6-9 show a third embodiment of the enema nozzle 1" according to the present invention. Said embodiment corresponds to the embodiment shown in FIGS. 1-4, and for like parts the same reference numbers are used. In the third embodiment the expandable loop 7 is substituted with a resilient compressible foam body 21 which can be moved out of the internal channel 8 of the catheter 2 in response to an operation of the control unit 10.

Figure 9:
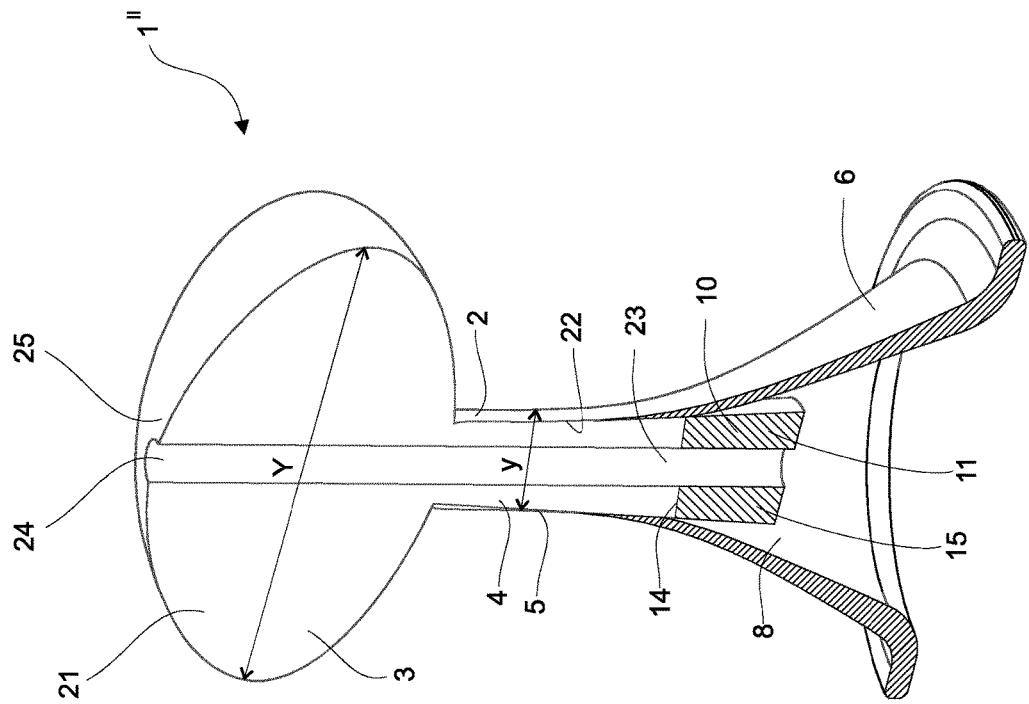
Figure 8:
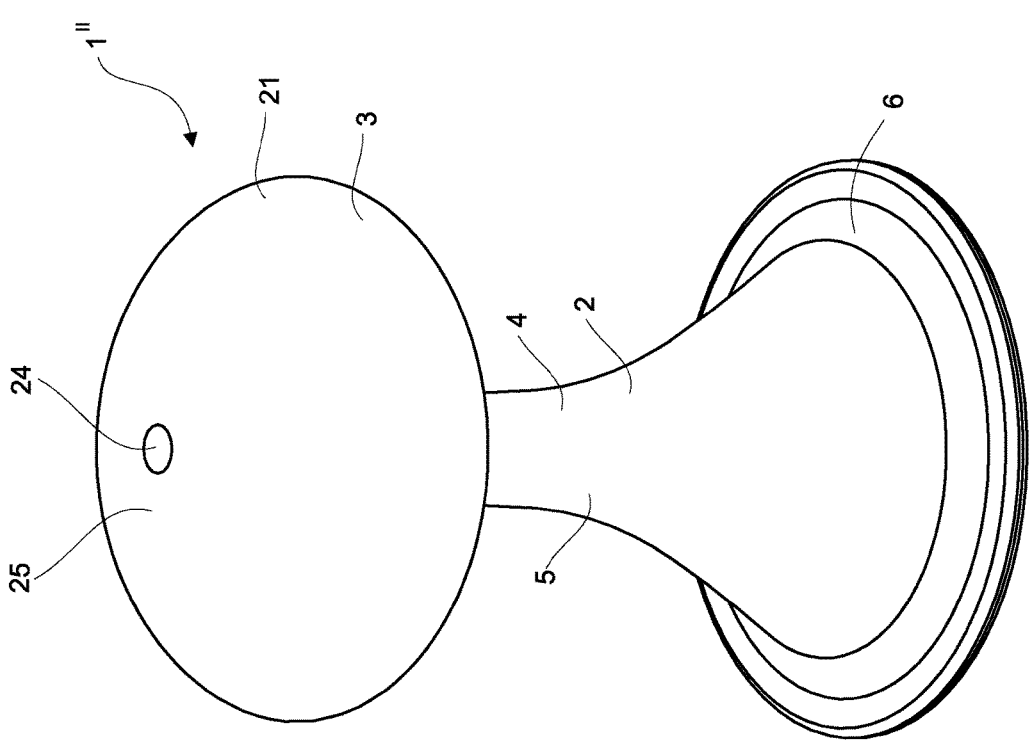

The foam body 21 is made of a compressible material which is compressed by the inner walls 22 of the internal channel 8, as shown in FIG. 9, and which automatically will expand when it is forced out of the internal channel 8 e.g. when it comes into contact with a liquid, e.g. the body fluids/humidity in the body cavity. In FIG. 7 the foam body 21 is partly out of the internal channel 8, and in FIG. 8 and FIG. 9 the foam body 21 is placed in the fully expanded position, where the largest direct distance Y (diameter) of the retention member is above four to five times the diameter y of the tip of the catheter 2.

As is best seen in FIG. 9 the enema flow channel 23 that extends through the cylinder 11 of the control unit 10 ends in a delivery opening 24 at the distal end 25 (top) of the foam body 21. However, in an alternative embodiment the flow channel may be terminated inside the foam body 21 for delivering the enema via the porous structure of the foam body. Such an embodiment is especially relevant if the body tissue is inflamed or otherwise damaged, as the pressure from enema liquid will be distributed over a larger area, thereby reducing any discomfort that the user might otherwise experience.

Figure 11:
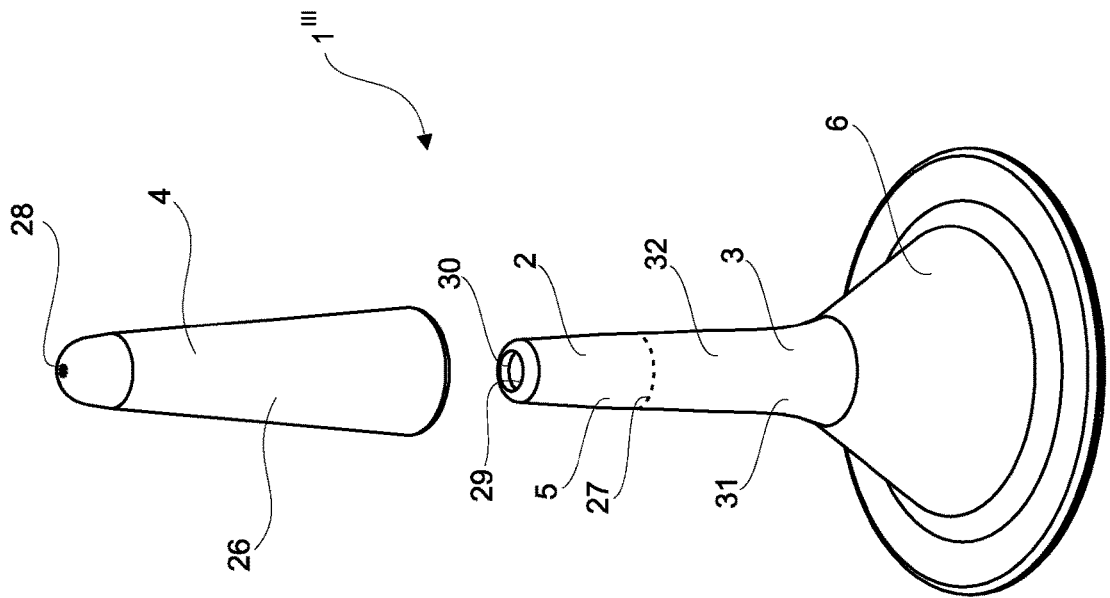
FIGS. 10-12 shows a fourth embodiment of an enema nozzle according to the present invention.
Figure 10:
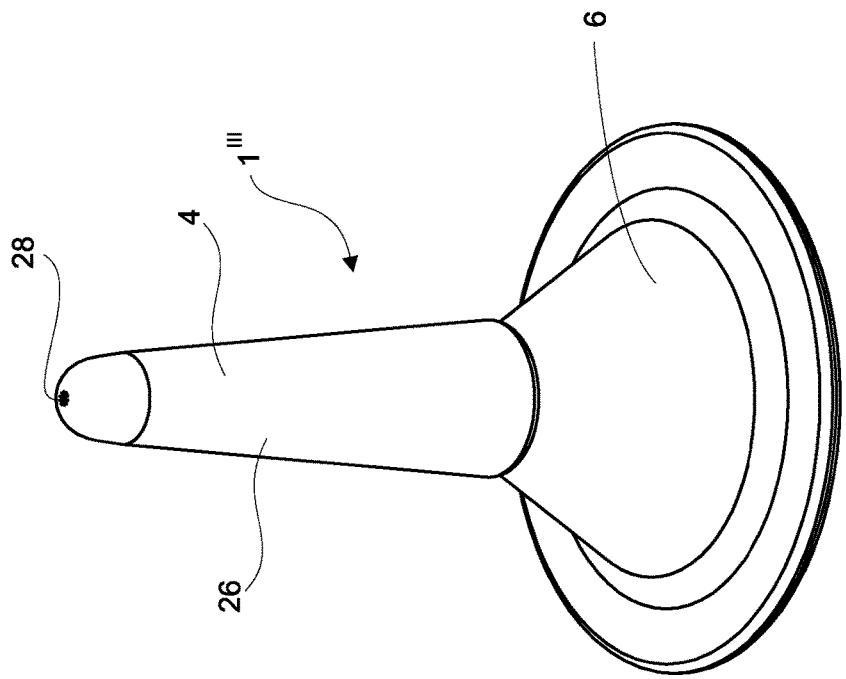
Figure 12:
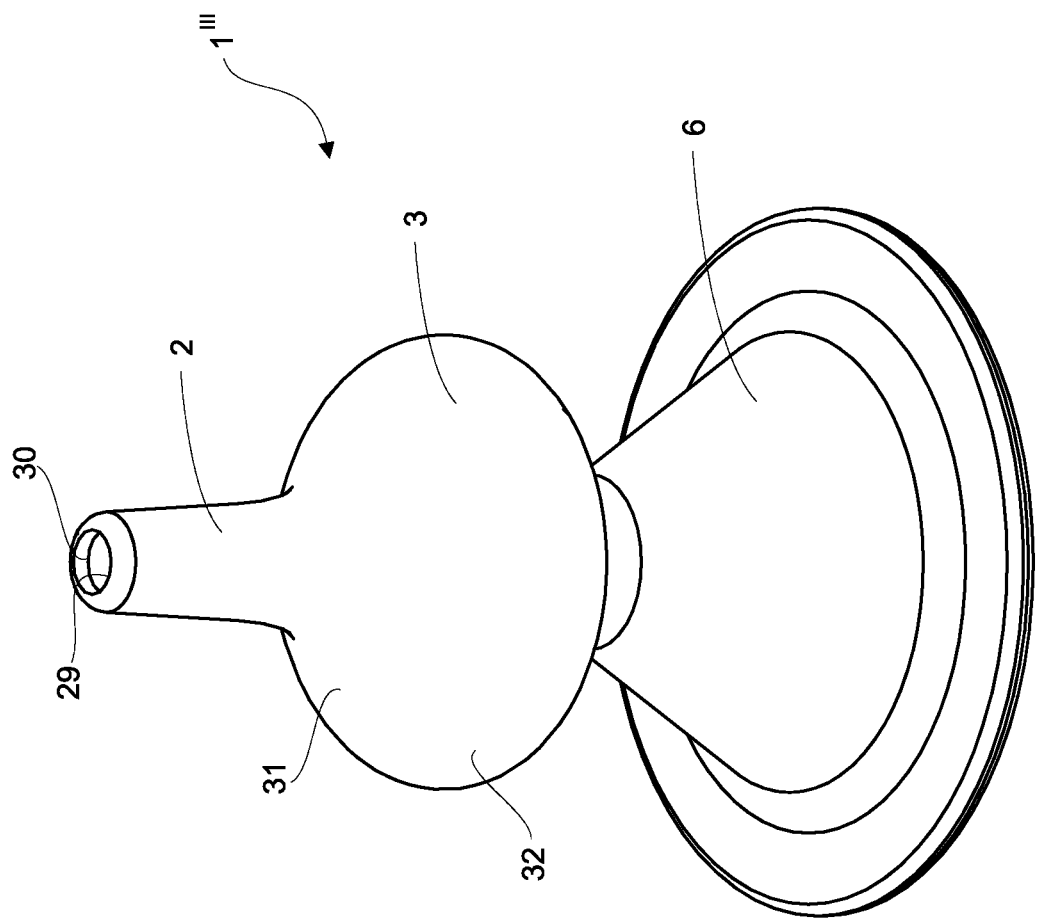

In a fourth embodiment shown in FIGS. 10-12 the restriction unit 4 is made of a thin cover 26 of a biodegradable material that will rapidly dissolve and/or disintegrate upon contact with a liquid/humidity. Said cover 26 is placed over the retention member 3 which as shown in FIG. 11 is arranged on the outer surface 27 of the catheter 2, such that the outer circumference of the retention member 3 in its compact form is substantially the same as the outer circumference of the catheter 2. The retention member is a foam body 31 which automatically will expand when it comes into contact with a liquid, e.g. the body fluids/humidity in the body cavity.

Before and during insertion the cover 26 restricts the size of the foam body 31, thereby providing an easy insertion without any discomfort due to extending and/or protection parts. Since it is preferred that the biodegradable cover 26 is dissolved/disintegrated and the foam body 31 is placed in the expanded form in less than two minutes, preferably less than one minute, the cover 26 comprises an small aperture 28 at the distal end of the cover, allowing the enema liquid to be expelled from said aperture 28, via the flow channel 29 and delivery opening 30 whereby the enema liquid may assist in dissolving/dintergrating the cover 26 and/or expand the foam body 31.

Once the restriction unit 26 is dissolved/disintegrated the foam body 31 may be allowed to expand to the expanded form, as shown in FIG. 12. Since the retention member is only placed in a middle section 32 of the catheter 2, the distal end 33 of the catheter 2 is not expanded.

In order to protect the biodegradable cover 26 before use, the enema nozzle may be stored in a gas-impermeable packaging, e.g. made of a laminate with an intermittent aluminum foil layer.

A number of alternative retention members are shown in FIG. 13, FIGS. 16-18. Said retention members correspond to the retention members discussed earlier and for like parts, the same reference numbers are use.

The retention members can further all be placed in the compact form using a restriction unit corresponding to the restriction unit shown in FIGS. 1-9, i.e. a restriction unit defined by an internal channel of the catheter which extends into a distal opening, and wherein the retention member is arranged for being movably in and/or out of said internal channel e.g. by means of a control unit, or a biodegradable restriction unit e.g. as discussed in FIGS. 10-12, i.e. a unit made of biodegradable material that will rapidly dissolve and/or disintegrate upon contact with a liquid/humidity.

Figure 13:
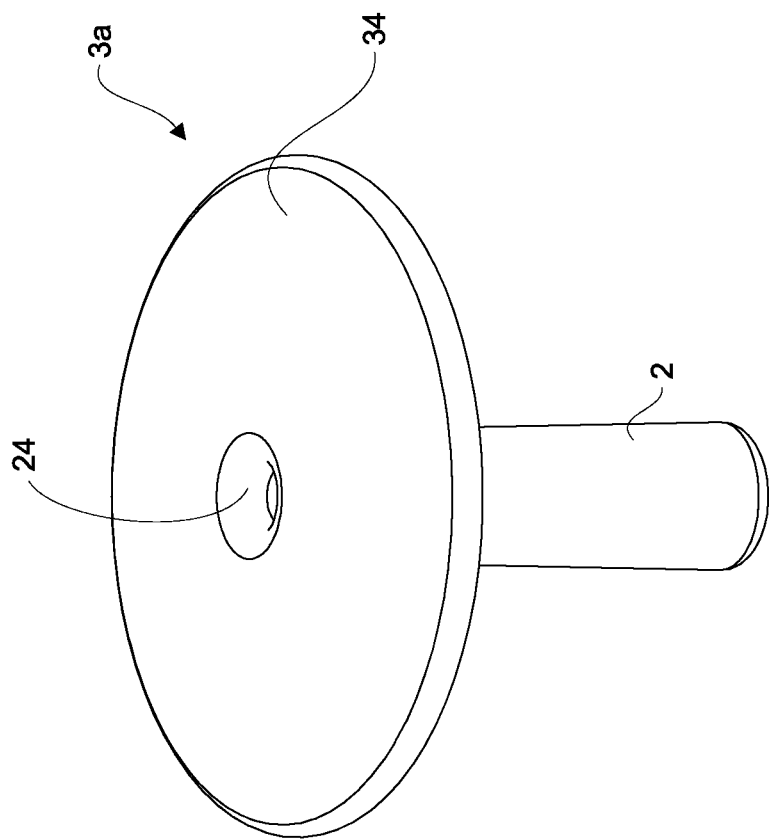
FIG. 13 shows a first alternative embodiment of a retention member.

FIG. 13 show a first alternative embodiment of a retention member 3a in the form of a foam body comprising a single disc 34, arranged such that said retention member 3a in the expanded form have an umbrella/mushroom shape wherein the disc 34 represents the canopy/cap and the catheter 2 the stem.

Figure 14:
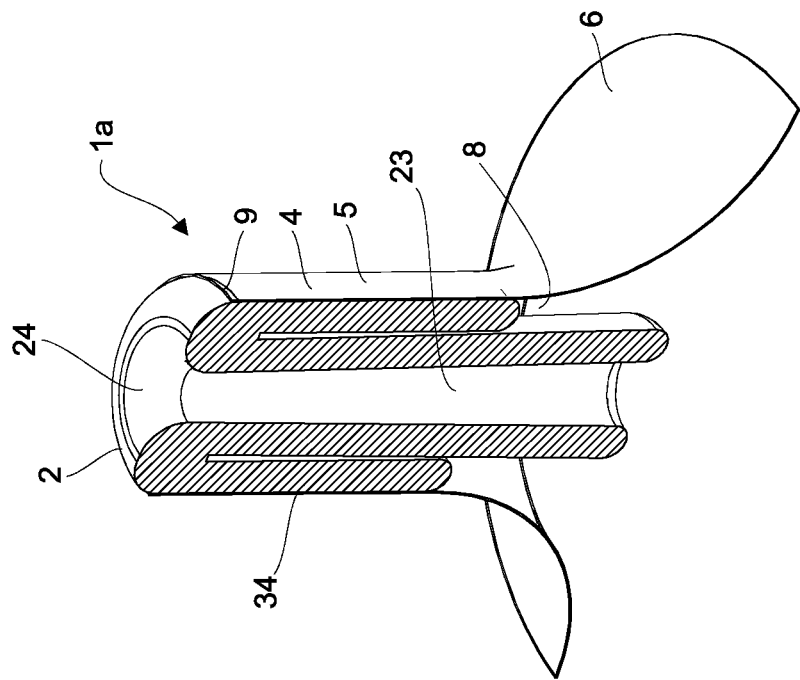
FIG. 14 shows the retention member of FIG. 13 placed in a first restriction unit.

In FIG. 14 the retention member 3a of FIG. 13 is placed in the compact form by a restriction unit 4 defined by an internal channel 8 of the catheter 2 which extends into a distal opening 9, and wherein the retention member 3a is arranged for being movably in and/or out of said internal channel 8 such that the retention member 3a projects from and/or withdraws into the distal opening 9 of the catheter 2 by means of a control unit (not shown), but the control unit may e.g. correspond to the control unit of FIG. 1-4.

As is shown in FIG. 14 the disc 34 is in the compact form folded and pressed against the inner side of the restriction unit 4, and an enema flow channel 23 extends through the catheter/restriction unit 4, and ends in a delivery opening 24 at the distal end (top) of the disc 34.

As an alternatively to having the retention member 3a being placed in the compact form by the restriction unit 4 shown in FIG. 14, the retention member 3a could alternatively be retained by a restriction unit 4 in the form of a small band 35 that holds the disc 34 in a folded compact form parallel with the outer side of the catheter 2, as shown in FIG. 15. Said band 35 is made of a biodegradable material that will dissolve and/or disintegrate upon contact with a liquid/humidity.

Before and during insertion the band 35 restricts the size of the retention member 3a, thereby providing an easy insertion without any discomfort due to extending and/or protection parts. Once the band 35 is dissolved/disintegrated the retention member 3a may be allowed to expand to the expanded form, as shown in FIG. 13.

When the band 35 of FIG. 15 is dissolved/disintegrated (or the retention member 3a is clear of the internal channel 8 of the catheter 2 of FIG. 14), the disc 34 will automatically expand axially in an outwardly direction to place the retention member in the expanded form shown in FIG. 13.

The retention member 3a can be made of any suitable material, e.g. foam or an elastomeric polymer.

In the embodiment of FIG. 16 the retention member 3b comprises a number of circular discs 36, and wherein the diameter of each discs (starting form the distal end 37 of the retention member) increases gradually towards the proximal end 38. In this way a disc 36a in the middle section of the retention member will have a diameter which is slightly smaller than the disc 36b placed below, but larger than the disc 36c placed above. In this way the retention member 3b has a shape resembling a Christmas-tree. In the embodiment shown the retention member 3b comprises five discs, but said number may be higher or lower if considered relevant.

The discs 36 of the retention member 3b may be restricted and expanded in a similar way as discussed for the embodiment 3a, and shown in FIGS. 14 and 15.

Figure 17:
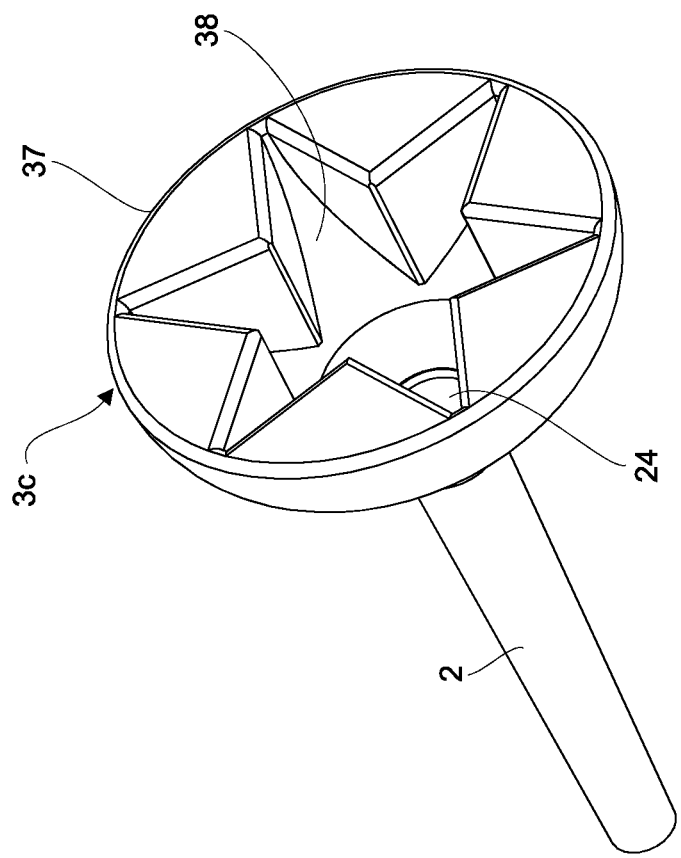
FIG. 17 shows a third alternative embodiment of a retention member.

In FIG. 17 the retention member 3c is in the form of an inverted soft cone 37, e.g. made of a form, with a cut away section 38 in the form of a star. Said cut-away section 38 ensures that the inverted soft cone both can be placed in the compact form during insertion and that it can collapse during removal. The inverted soft cone will both provide an efficient seal with the colon wall and feel comfortable for the user.

The discs 36 may be of either a foam material and/or an elastomeric polymer, in either case it will provides a seal with the colon wall when placed in the expanded form. One or more delivery openings may be provided between the discs.

The inverted soft cone 37 may be restricted and expanded in a similar way as discussed for the embodiment 3a, and shown in FIGS. 14 and 15.

Figure 18:
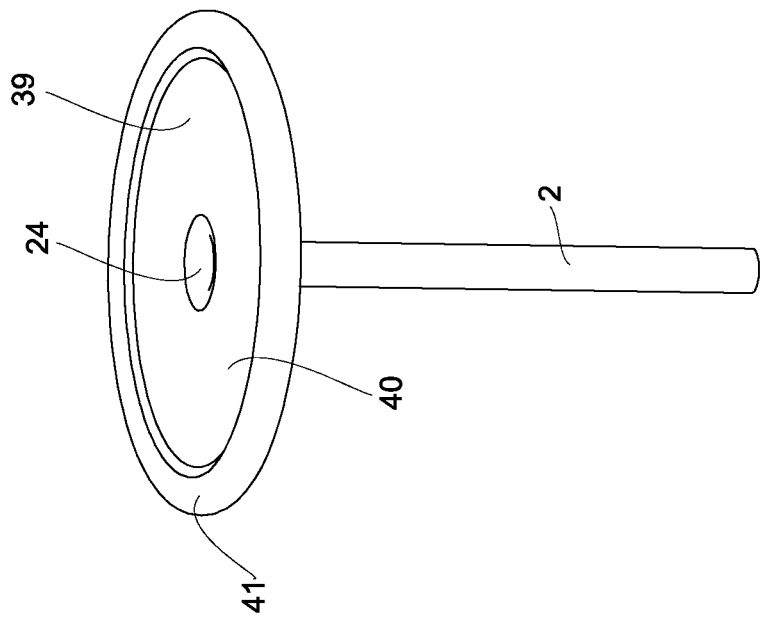
FIG. 18 shows an alternative embodiment of a retention member.

The embodiment 3d shown in FIG. 18 corresponds to the embodiment 3b shown in FIG. 13, but here the disc 39 consist of a thin (about 1-5 mm) canopy 40 made of a flexible elastomeric material with a soft foam ring 41 placed along the entire circumferences. The soft ring 41 will provides a tight fit with the colon wall and efficiently prevent premature and unwanted leakage of fluid and fecal matter from the anus during an irrigation session. The thin canopy 40 will ensure that the retention member 3d easily can be placed in the compact form, where it will take up very little space, or expanded form, but also that it easily will fold upwards, when the enema device is pulled out, or the retention member is retracted into the restriction unit (internal channel of the catheter).

The retention member 3d may be restricted and expanded in a similar way as discussed for the embodiment 3a, and shown in FIGS. 14 and 15.

Figure 19:
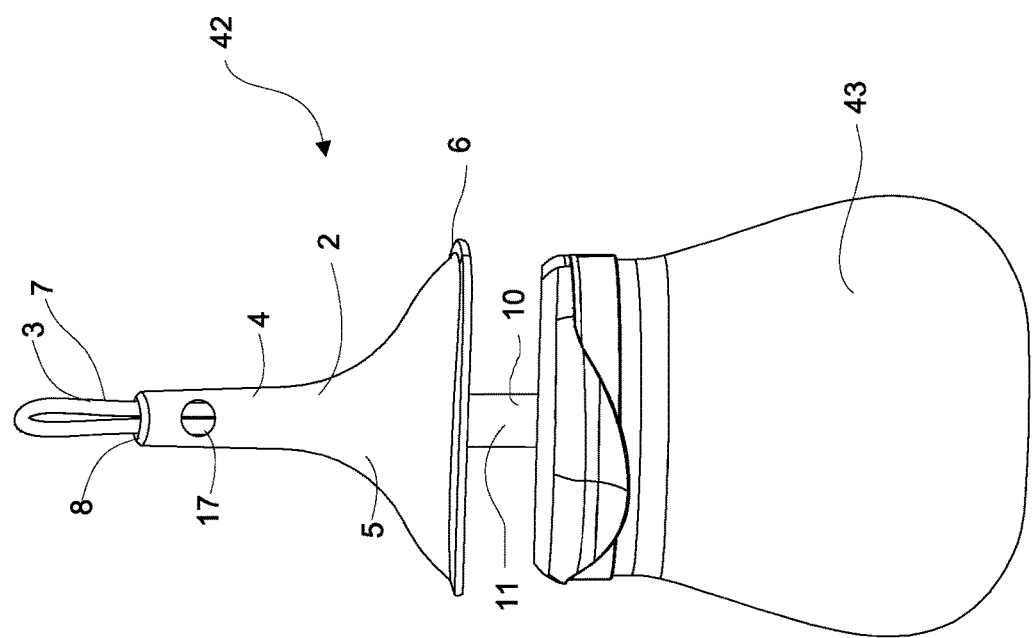
FIG. 19 shows a perspective view of an enema system comprising the enema nozzle shown in FIGS. 1-4.

FIG. 19 shows an enema system 42 according to the invention, wherein the enema nozzle shown in FIGS. 1-4 is connected to a substantially bulb-formed enema delivery container 43, arranged for containing the enema. The enema is administered by squeezing the delivery container 43 one or more times, depending on the desired dosage. The enema system 42 may comprises a one-way valve (not shown) that effectively will prevent backflow of liquid and faeces from the colon and/or rectum into the device and said one-way valve will therefore preclude any contamination of the delivery container 43 and it's remaining content, which may occur after administration of the enema to a patient. Furthermore, since backflow efficiently is prevented, the delivery container can easily be used for several applications, e.g. by refilling the container with a second dose of the same—or a different—enema (liquid).

The enema nozzle 1 may be removable connected to the delivery container by means of a coupling (not shown). Thereby can the enema nozzle be a disposable nozzle or the nozzle can be individually cleaned and/or sterilised. The delivery container may be reused several times.

The enema nozzles disclosed herein may also be used for larger irrigations systems wherein the enema nozzle is connected to the enema reservoir via a relatively long delivery tube, and wherein the irrigation system e.g. comprises pumping means, control means, collection means for the stool, etc.

Modifications and combinations of the above principles and designs are foreseen within the scope of the present invention.

The invention claimed is:

1. An enema nozzle for an enema system, and wherein said enema nozzle comprises a catheter provided with a retention member, said retention member is arranged for being placed in a compact form during insertion in a body cavity and for being placed in an expanded form for retaining the enema nozzle in said body cavity after insertion, and wherein the enema nozzle further comprises a restriction unit arranged for placing the retention member in its compact form during insertion, and wherein the restriction unit, an internal channel in the catheter, is arranged for at least partly surrounding/encompassing the retention member during insertion in the body cavity, and wherein the enema nozzle comprises a one-way valve arranged for preventing backflow into the enema nozzle, and wherein the restriction unit and the catheter are an integral, single unit.

2. The enema nozzle according to claim 1, wherein the restriction unit and the retention member are arranged for being displaced in relation to each other after the enema nozzle has been inserted in the body cavity, and/or the restriction unit is configured for being at least partly removed from the retention member after the enema nozzle has been inserted in the body cavity, thereby allowing the retention member to expand for retaining the enema nozzle in said body cavity.

3. The enema nozzle according to claim 1, wherein the restriction unit is arranged for conforming the retention member to a shape and/or dimensions of the catheter when the retention member is in the compact form; and/or for preventing the retention member from extending and/or projecting from an annular outer longitudinal side/surface of the catheter.

4. The enema nozzle according to claim 1, wherein an outer circumference of the retention member in its compact form is the same, substantially the same or less than an outer circumference of the catheter.

5. The enema nozzle according to claim 1, wherein the retention member is not a balloon arranged for being inflated with air or liquid.

6. The enema nozzle according claim 1, wherein the retention member in its compact form is arranged in parallel with a longitudinal axis of the catheter, and extends outwardly from said catheter in its expanded form.

7. The enema nozzle according to claim 1, wherein the retention member and the catheter are different elements.

8. The enema nozzle according to claim 1, wherein the restriction unit is configured such that the retention member will not expand, at least completely, until after the catheter is substantially fully inserted.

9. The enema nozzle according to claim 1, wherein the retention member is arranged for being movably in and/or out of said internal channel such that the retention member projects from and/or withdraws into a distal opening of the catheter.

10. The enema nozzle according to claim 9, wherein the enema nozzle comprises a control unit arranged for in a first position placing the retention member in the compact form, and in a second position placing the retention member in the expanded form.

11. The enema nozzle according to claim 10, wherein the control unit comprises a cylinder arranged for being axially displaced inside the internal channel in a longitudinal direction of the catheter.

12. The enema nozzle according to claim 10, wherein the control unit comprises an internal flow channel which ends in one or more first delivery openings, and wherein said one or more first delivery openings are in fluid communication with corresponding second delivery openings arranged in a side wall of the catheter.

13. The enema nozzle according to claim 1, wherein the retention member is made of an elastic material.

14. The enema nozzle according to claim 1, wherein the retention member comprises an expandable loop.

15. The enema nozzle according to claim 14, wherein ends of the expandable loop is attached to a control unit so that the ends of the expandable loop either concurrently or individually can be moved to alter a shape of the expandable loop outside a distal opening of the catheter.

16. The enema nozzle according to claim 14, wherein the expandable loop is a tube arranged for delivering an enema via one or more openings placed in the side wall of said tube.

17. The enema nozzle according to claim 1, wherein the retention member comprises a foam body.

18. The enema nozzle according to claim 17, wherein the foam body is made of a compressible material and/or a material that will expand when it comes into contact with a liquid.

19. The enema nozzle according to claim 17, wherein an enema is administered to the rectum/colon via the foam body.

20. The enema nozzle according to claim 1, wherein the retention member comprises a number of expandable wings/arms and/or discs arranged in parallel with a longitudinal axis of the catheter in the compact form, and in the expanded form extend radially outwardly from the catheter.

21. The enema nozzle according to claim 20, wherein the retention member comprises at least one disc and which in the expanded form has a form corresponding to a mushroom/umbrella, or a Christmas tree.

22. The enema nozzle according to claim 1, wherein the restriction unit comprises a number of openings/slots.

23. An enema nozzle for an enema system, and wherein said enema nozzle comprises a catheter provided with a retention member, said retention member is arranged for being placed in a compact form during insertion in a body cavity and for being placed in an expanded form for retaining the enema nozzle in said body cavity after insertion, and wherein the enema nozzle further comprises a restriction unit arranged for placing the retention member in its compact form during insertion, and wherein the restriction unit is arranged for at least partly surrounding/encompassing the retention member during insertion in the body cavity, and wherein the enema nozzle comprises a one-way valve arranged for preventing backflow into the enema nozzle, and wherein the restriction unit comprises an opening arranged for delivering enema via the opening.

* * * * *